(12) United States Patent
Bouyssou et al.

(10) Patent No.: US 7,405,232 B2
(45) Date of Patent: Jul. 29, 2008

(54) LONG ACTING BETA-2 AGONISTS AND THEIR USE AS MEDICAMENTS

(75) Inventors: Thierry Bouyssou, Mietingen (DE); Christoph Hoenke, Ingelheim (DE); Ingo Konetzki, Warthausen (DE); Juergen Mack, Biberach (DE); Andreas Schnapp, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 508 days.

(21) Appl. No.: 11/057,893

(22) Filed: Feb. 14, 2005

(65) Prior Publication Data

US 2005/0197374 A1 Sep. 8, 2005

Related U.S. Application Data

(60) Provisional application No. 60/557,078, filed on Mar. 26, 2004.

(30) Foreign Application Priority Data

Feb. 14, 2004 (EP) .................. 04003354

(51) Int. Cl.
*A61K 31/41* (2006.01)
*C07D 249/08* (2006.01)
(52) U.S. Cl. .................. 514/383; 548/262.2
(58) Field of Classification Search .......... 514/383; 548/262.2
See application file for complete search history.

(56) References Cited

U.S. PATENT DOCUMENTS

| | | | |
|---|---|---|---|
| 4,378,361 A | 3/1983 | Schromm et al. | |
| 4,581,367 A | 4/1986 | Schromm et al. | |
| 4,647,563 A | 3/1987 | Schromm et al. | |
| 7,214,698 B2 * | 5/2007 | Trieselmann et al. | ....... 514/399 |
| 2002/0022625 A1 | 2/2002 | Walland et al. | |
| 2004/0127733 A1 | 7/2004 | Trieselmann et al. | |

FOREIGN PATENT DOCUMENTS

| | | |
|---|---|---|
| CA | 2 405 745 A1 | 11/2001 |
| CA | 2 504 213 A1 | 5/2004 |
| EP | 0008653 | 3/1980 |
| WO | WO 01/83462 | 11/2001 |
| WO | WO 2004/039784 | 5/2004 |

OTHER PUBLICATIONS

Copending U.S. Appl. No. 11/118,295.*
Ali et al., J. Pharmacology and Experimental Therapeutics, vol. 268, No. 3, 1993.*
Information Disclosure Statement for PCT/EP2005/001232 mailed on Apr. 24, 2005.

* cited by examiner

*Primary Examiner*—Golam M. M. Shameem
*Assistant Examiner*—Susannah Chung
(74) *Attorney, Agent, or Firm*—Michael P. Morris; Edouard G. Lebel

(57) ABSTRACT

A compound of formula 1

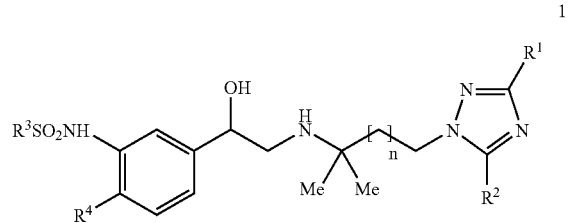

wherein the groups $R^1$, $R^2$, $R^3$, $R^4$ and n may have the meanings given in the claims and in the specification, and methods for preparing a pharmaceutical composition for the treatment of inflammatory and obstructive respiratory complaints.

16 Claims, No Drawings

LONG ACTING BETA-2 AGONISTS AND THEIR USE AS MEDICAMENTS

RELATED APPLICATIONS

This application claims the benefit under 35 USC 119(a) of European Patent Application 04003354, filed on Feb. 14, 2004, which application is incorporated herein in its entirety. This application also claims the benefit under 35 USC 119(e) of U.S. Provisional Application Ser. No. 60/557,078, filed on Mar. 26, 2004, which application is incorporated herein in its entirety.

BACKGROUND TO THE INVENTION

1. Field of the Invention

The present invention relates to the use of compounds of formula 1

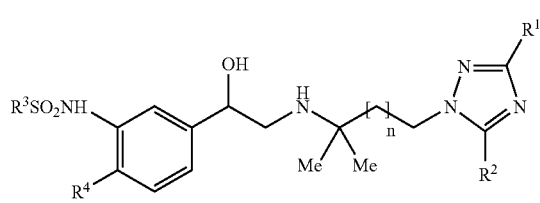

wherein the groups $R^1$, $R^2$, $R^3$, $R^4$ and n may have the meanings given in the claims and in the specification, for preparing a pharmaceutical composition for the treatment of inflammatory and obstructive respiratory complaints, and new compounds of formula 1, per se.

2. Description of the Prior Art

Betamimetics (β-adrenergic substances) are known from the prior art.

For the drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the wellbeing of the patient to a high degree.

It is particularly desirable to prepare a pharmaceutical composition that can be used therapeutically by administration once a day (single dose). The use of a drug once a day has the advantage that the patient can become accustomed relatively quickly to regularly taking the drug at certain times of the day.

The aim of the present invention is therefore to provide betamimetics that are characterized by a longer duration of activity and can thus be used to prepare pharmaceutical compositions with a longer duration of activity. A particular aim of the invention is to prepare betamimetics that, by virtue of their long-lasting effect, can be used to prepare a drug for administration once a day. A further objective of the invention is to prepare new betamimetics that, by virtue of their long-lasting effect, can be used to prepare a drug for administration once a day for the treatment of inflammatory or obstructive respiratory complaints. In addition to the above objectives, the present invention also sets out to provide betamimetics that are not only exceptionally potent but are also characterized by a high degree of selectivity with respect to the $β_2$-adreno-receptor.

DESCRIPTION OF THE INVENTION

Surprisingly it has been found that the above-mentioned objectives are achieved by compounds of formula 1. Accordingly, the present invention relates to the use of compounds of formula 1

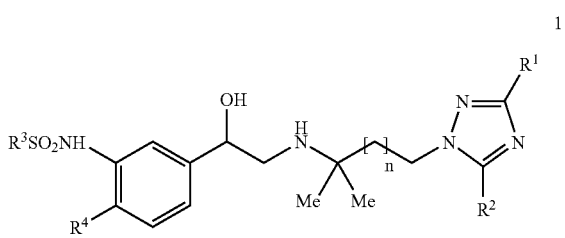

wherein
$R^1$ denotes hydrogen, —$C_{1-6}$-alkyl, —$C_{1-6}$-haloalkyl, —OH, —O—$C_{1-6}$-alkyl, halogen, aryl, or a heterocycle, optionally substituted by 1, 2, 3, 4, or 5 identical or different groups $R^5$;
$R^2$ denotes hydrogen, —$C_{1-6}$-alkyl, —$C_{1-6}$-haloalkyl; preferably methyl;
$R^3$ denotes —$C_{1-6}$-alkyl; preferably methyl;
$R^4$ denotes —OH, —$NH_2$, halogen; preferably —OH;
$R^5$ denotes halogen, —CN, —$NO_2$, —$C_{1-6}$-alkyl, —$C_{3-6}$-cycloalkyl, —$C_{1-6}$-haloalkyl, —$COR^6$, —$COOR^6$, —$CONR^6R^7$, —$OR^6$, —$NR^6R^7$, —$NR^6COR^7$, —$NR^6SO_2R^7$, —$SR^6$, —$SOR^6$, —$SO_2R^6$ or —$SO_2NR^6R^7$, or two $R^5$ joined together denote a group selected from —$C_{2-6}$-alkylene, —$C_{2-6}$-alkenylene and —O—$C_{1-6}$-alkylene-O—;
$R^6$ and $R^7$ denotes hydrogen, —$C_{1-6}$-alkyl, —$C_{3-6}$-cycloalkyl;
n denotes 0, 1, 2 or 3; preferably 1;

optionally in the form of the individual optical isomers, mixtures of the individual enantiomers or racemates, in the form of the free bases or the corresponding acid addition salts with pharmacologically acceptable acids, for preparing a pharmaceutical composition for the treatment of inflammatory and obstructive respiratory complaints.

It is preferable to use compounds of formula 1 as stated above wherein $R^1$, $R^2$, $R^3$, and n are as hereinbefore defined and
$R^4$ denotes —OH optionally in the form of the individual optical isomers, mixtures of the individual enantiomers or racemates, in the form of the free bases or the corresponding acid addition salts with pharmacologically acceptable acids.

It is particularly preferable to use compounds of formula 1 as stated above wherein $R^2$, $R^3$, $R^4$, and n are as hereinbefore defined and
$R^1$ denotes hydrogen, —$C_{1-6}$-alkyl, —$C_{1-6}$-haloalkyl, —OH, —O—$C_{1-6}$-alkyl, halogen or aryl, if possible optionally substituted by 1, 2, 3, 4 or 5 identical or different groups $R^5$;
$R^5$ denotes halogen, —CN, —$NO_2$, —$C_{1-6}$-alkyl, —$C_{3-6}$-cycloalkyl, —$C_{1-6}$-haloalkyl, —$COR^6$, —$COOR^6$, —$CONR^6R^7$, —$OR^6$, —$NR^6R^7$, —$NR^6COR^7$, —$NR^6SO_2R^7$, —$SR^6$, —$SOR^6$, —$SO_2R^6$ or —$SO_2NR^6R^7$, or two $R^5$ joined together denote a group selected from —$C_{2-6}$-alkylene, —$C_{2-6}$-alkenylene and —O—$C_{1-6}$-alkylene-O—;
$R^6$ and $R^7$ denote hydrogen, —$C_{1-6}$-alkyl, —$C_{3-6}$-cycloalkyl;

optionally in the form of the individual optical isomers, mixtures of the individual enantiomers or racemates, in the form of the free bases or the corresponding acid addition salts with pharmacologically acceptable acids.

It is particularly preferable to use compounds of formula 1, as stated above, wherein
$R^1$ denotes hydrogen, —$C_{1-6}$-alkyl, —O—$C_{1-6}$-alkyl, aryl, if possible optionally substituted by 1, 2, 3, 4, or 5 identical or different groups $R^5$;
$R^2$ denotes hydrogen, —$C_{1-6}$-alkyl; preferably methyl;
$R^3$ denotes methyl;
$R^4$ denotes —OH;
$R^5$ denotes halogen, —CN, —$NO_2$, —$C_{1-6}$-alkyl, —$C_{3-6}$-cycloalkyl, —$C_{1-6}$-haloalkyl, —$COR^6$, —$COOR^6$, —$CONR^6R^7$, —$OR^6$, —$NR^6R^7$, —$NR^6COR^7$, —$NR^6SO_2R^7$, —$SR^6$, —$SOR^6$, —$SO_2R^6$ or —$SO_2NR^6R^7$, or two $R^5$ joined together denote a group selected from —$C_{2-6}$-alkylene, —$C_{2-6}$-alkenylene and —O—$C_{1-6}$-alkylene-O—;
$R^6$ and $R^7$ denote hydrogen, —$C_{1-6}$-alkyl, —$C_{3-6}$-cycloalkyl;
n denotes 0, 1, 2 or 3; preferably 1;

optionally in the form of the individual optical isomers, mixtures of the individual enantiomers or racemates, in the form of the free bases or the corresponding acid addition salts with pharmacologically acceptable acids.

It is particularly preferable to use compounds of formula 1 as stated above wherein
$R^1$ denotes hydrogen, aryl, if possible optionally substituted by 1, 2, 3, 4, or 5 identical or different groups $R^5$;
$R^2$ denotes hydrogen, —$C_{1-6}$-alkyl; preferably methyl;
$R^3$ denotes methyl;
$R^4$ denotes —OH;
$R^5$ denotes halogen, —CN, —$NO_2$, —$C_{1-6}$-alkyl, —$C_{3-6}$-cycloalkyl, —$C_{1-6}$-haloalkyl, —$COR^6$, —$COOR^6$, —$CONR^6R^7$, —$OR^6$, —$NR^6R^7$, —$NR^6COR^7$, —$NR^6SO_2R^7$, —$SR^6$, —$SOR^6$, —$SO_2R^6$ or —$SO_2NR^6R^7$, or two $R^5$ joined together denote a group selected from —$C_{2-6}$-alkylene, —$C_{2-6}$-alkenylene and —O—$C_{1-6}$-alkylene-O—;
$R^6$ and $R^7$ denotes hydrogen, —$C_{1-6}$-alkyl, —$C_{3-6}$-cycloalkyl;
n denotes 0, 1, 2 or 3; preferably 1;

optionally in the form of the individual optical isomers, mixtures of the individual enantiomers or racemates, in the form of the free bases or the corresponding acid addition salts with pharmacologically acceptable acids.

It is particularly preferable to use compounds of formula 1 as stated above wherein
$R^1$ denotes hydrogen, phenyl, optionally substituted by 1, 2, 3, 4, or 5 identical or different groups $R^5$;
$R^2$ denotes hydrogen, ethyl, methyl; preferably methyl or ethyl;
$R^3$ denotes methyl;
$R^4$ denotes OH;
$R^5$ denotes halogen, —CN, —$NO_2$, —$C_{1-6}$-alkyl, —$C_{3-6}$-cycloalkyl, —$C_{1-6}$-haloalkyl, —$COR^6$, —$COOR^6$, —$CONR^6R^7$, —$OR^6$, —$NR^6R^7$, —$NR^6COR^7$, —$NR^6SO_2R^7$, $SR^6$, —$SOR^6$, —$SO_2R^6$ or —$SO_2NR^6R^7$, or two $R^5$ joined together denote a group selected from —$C_{2-6}$-alkylene, —$C_{2-6}$-alkenylene and —O—$C_{1-6}$-alkylene-O—;
$R^6$ and $R^7$ denote hydrogen, —$C_{1-6}$-alkyl, —$C_{3-6}$-cycloalkyl;
n denotes 1;

optionally in the form of the individual optical isomers, mixtures of the individual enantiomers or racemates, in the form of the free bases or the corresponding acid addition salts with pharmacologically acceptable acids.

It is particularly preferable to use the compounds of general formula 1 as detailed above for preparing a pharmaceutical composition for the treatment of respiratory complaints selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome), and all forms of pulmonary oedema.

The compounds are preferably used for preparing a pharmaceutical composition for the treatment of obstructive pulmonary diseases selected from among bronchial asthma, paediatric asthma, severe asthma, acute asthma attacks, chronic bronchitis, and COPD (chronic obstructive pulmonary disease), while it is particularly preferable according to the invention to use them for preparing a pharmaceutical composition for the treatment of bronchial asthma (optionally also referred to only as asthma within the scope of the present invention) and COPD.

It is also preferable to use the compounds as detailed above for preparing a pharmaceutical composition for the treatment of pulmonary emphysema that has its origins in COPD or α1-proteinase inhibitor deficiency.

It is also preferable to use the compounds as detailed above for preparing a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as, for example, lymphangiosis carcinomatosa, bronchoalveolar carcinoma, and lymphomas.

It is also preferable to use the compounds as detailed above for preparing a pharmaceutical composition for the treatment of interstitial pulmonary diseases selected from among pneumonia caused by infections, such as, for example, infection by viruses, bacteria, fungi, protozoa, helminthes, or other pathogens, pneumonitis caused by various factors, such as, for example, aspiration and left heart insufficiency, radiation-induced pneumonitis or fibrosis, collagenoses, such as, for example, lupus erythematodes, systemic sclerodermy, or sarcoidosis, granulomatoses, such as, for example, Boeck's disease, idiopathic interstitial pneumonia, or idiopathic pulmonary fibrosis (IPF).

It is also preferable to use the compounds detailed above for preparing a pharmaceutical composition for the treatment of cystic fibrosis or mucoviscidosis.

It is also preferable to use the drug combinations according to the invention for preparing a pharmaceutical composition for the treatment of bronchitis, such as, for example, bronchitis caused by bacterial or viral infection, allergic bronchitis, and toxic bronchitis.

It is also preferable to use the compounds detailed above for preparing a pharmaceutical composition for the treatment of bronchiectasis.

It is also preferable to use the compounds detailed above for preparing a pharmaceutical composition for the treatment of ARDS (adult respiratory distress syndrome).

It is also preferable to use the compounds detailed above for preparing a pharmaceutical composition for the treatment of pulmonary oedema, for example toxic pulmonary oedema after aspiration or inhalation of toxic substances and foreign substances.

It is particularly preferable to use the compounds detailed above for preparing a pharmaceutical composition for the treatment of asthma or COPD. Also of particular importance is the above-mentioned use of the drug combinations according to the invention for preparing a pharmaceutical composition for once-a-day treatment of inflammatory and obstructive respiratory complaints, particularly for the once-a-day treatment of asthma or COPD.

The invention also relates to new compounds of formula 1 per se. In particular the present invention relates to new compounds of formula 1 wherein $R^1$, $R^2$, and n may have the meanings given above, and wherein $R^3$ denotes methyl and $R^4$ denotes OH, optionally in the form of the individual optical isomers, mixtures of the individual enantiomers or racemates, in the form of the free bases or the corresponding acid addition salts with pharmacologically acceptable acids.

Preferred are compounds of formula 1, wherein $R^1$ and n may have the meanings given above, and wherein
$R^2$ denotes methyl or ethyl;
$R^3$ denotes methyl; and
$R^4$ denotes OH, optionally in the form of the individual optical isomers, mixtures of the individual enantiomers or racemates, in the form of the free bases or the corresponding acid addition salts with pharmacologically acceptable acids.

Also preferred are compounds of formula 1, wherein $R^1$ may have the meanings given above, and wherein
$R^2$ denotes methyl or ethyl;
$R^3$ denotes methyl;
$R^4$ denotes OH; and
n denotes 1, optionally in the form of the individual optical isomers, mixtures of the individual enantiomers or racemates, in the form of the free bases or the corresponding acid addition salts with pharmacologically acceptable acids.

Preferred according to the invention are compounds of formula 1, wherein
$R^1$ denotes hydrogen, phenyl, optionally substituted by 1, 2 or 3 identical or different groups $R^5$;
$R^2$ denotes methyl or ethyl, preferably methyl;
$R^3$ denotes methyl;
$R^4$ denotes OH;
$R^5$ denotes halogen, —$C_{1-6}$-alkyl, —$C_{3-6}$-cycloalkyl, —$C_{1-6}$-haloalkyl, —$COOR^6$, —$CONR^6R^7$, —$OR^6$, —$NR^6R^7$, —$NR^6COR^7$, —$NR^6SO_2R^7$ or two $R^5$ joined together denote a group selected from —$C_{2-6}$-alkylene, —$C_{2-6}$-alkenylene and —O—$C_{1-6}$-alkylene-O—;
$R^6$ and $R^7$ denote hydrogen, —$C_{1-6}$-alkyl, —$C_{3-6}$-cycloalkyl; and
n denotes 1;

optionally in the form of the individual optical isomers, mixtures of the individual enantiomers or racemates, in the form of the free bases or the corresponding acid addition salts with pharmacologically acceptable acids.

Also preferred are compounds of formula 1 wherein
$R^1$ denotes hydrogen, phenyl, optionally substituted by 1, 2 or 3 identical or different groups $R^5$;
$R^2$ denotes ethyl or methyl; preferably methyl;
$R^3$ denotes methyl;
$R^4$ denotes OH;
$R^5$ denotes halogen, —$C_{1-6}$-alkyl, —$C_{1-6}$-haloalkyl, —$COOR^6$, —$CONR^6R^7$, —$OR^6$, —$NR^6R^7$ or two $R^5$ joined together represent —O—$C_{1-6}$-alkylene-O—;
$R^6$ and $R^7$ denote hydrogen, —$C_{1-6}$-alkyl; and
n denotes 1;

optionally in the form of the individual optical isomers, mixtures of the individual enantiomers or racemates, in the form of the free bases or the corresponding acid addition salts with pharmacologically acceptable acids.

Particularly preferred are compounds of formula 1 wherein
$R^1$ denotes phenyl, optionally substituted by 1, 2 or 3 identical or different groups $R^5$;
$R^2$ denotes methyl, ethyl; preferably methyl;
$R^3$ denotes methyl;
$R^4$ denotes OH;
$R^5$ denotes chlorine, bromine, fluorine, methyl, ethyl, —$CF_3$, —COOH, —COOMe, —OH, or —OMe; and
n denotes 1, optionally in the form of the individual optical isomers, mixtures of the individual enantiomers or racemates, in the form of the free bases or the corresponding acid addition salts with pharmacologically acceptable acids.

Particularly preferred compounds of formula 1 are selected from the group consisting of:

N-[5-(2-{3-[5-ethyl-3-(4-methoxy-phenyl)-[1,2,4]triazol-1-yl]-1,1-dimethyl-propylamino}-1-hydroxy-ethyl)-2-hydroxy-phenyl]-methanesulphonamide;

N-[5-(2-{1,1-dimethyl-3-[5-methyl-3-(4-trifluoromethyl-phenyl)-[1,2,4]triazol-1-yl]-propylamino}-1-hydroxy-ethyl)-2-hydroxy-phenyl]-methanesulphonamide;

N-(5-{2-[1,1-dimethyl-3-(5-methyl-3-p-tolyl-[1,2,4]triazol-1-yl)-propylamino]-1-hydroxy-ethyl}-2-hydroxy-phenyl)-methanesulphonamide;

N-[5-(2-{3-[3-(4-fluoro-phenyl)-5-methyl-[1,2,4]triazol-1-yl]-1,1-dimethyl-propylamino)-1-hydroxy-ethyl)-2-hydroxy-phenyl]-methanesulphonamide;

methyl 3-(1-{3-[2-hydroxy-2-(4-hydroxy-3-methanesulphonylamino-phenyl)-ethylamino]-3-methyl-butyl}-5-methyl-1H-[1,2,4]triazol-3-yl)-benzoate;

N-[5-(2-{3-[3-(3,5-difluoro-phenyl)-5-methyl-[1,2,4]triazol-1-yl]-1,1-dimethyl-propylamino}-1-hydroxy-ethyl)-2-hydroxy-phenyl]-methanesulphonamide;

N-[2-hydroxy-5-(1-hydroxy-2-{3-[3-(2-methoxy-phenyl)-5-methyl-[1,2,4]triazol-1-yl]-1,1-dimethyl-propylamino}-ethyl)-phenyl]-methanesulphonamide;

N-[2-hydroxy-5-(1-hydroxy-2-{3-[3-(4-methoxy-phenyl)-5-methyl-[1,2,4]triazol-1-yl]-1,1-dimethyl-propylamino}-ethyl)-phenyl]-methanesulphonamide;

N-(5-{2-[3-(3-benzo[1,3]dioxol-5-yl-5-methyl-[1,2,4]triazol-1-yl)-1,1-dimethyl-propyl-amino]-1-hydroxy-ethyl}-2-hydroxy-phenyl)-methanesulphonamide;

N-[2-hydroxy-5-(1-hydroxy-2-{3-[3-(4-methoxy-phenyl)-[1,2,4]triazol-1-yl]-1,1-dimethyl-propylamino}-ethyl)-phenyl]-methanesulphonamide; and N-{5-[2-[1,1-dimethyl-3-[1,2,4]triazol-1-yl-propylamino)-1-hydroxy-ethyl]-2-hydroxy-ethyl]-2hydroxy-phenyl}-methanesulphonamide, optionally in the form of the individual optical isomers, mixtures of the individual enantiomers or racemates, in the form of the free bases or the corresponding acid addition salts with pharmacologically acceptable acids.

The compounds of formula 1 may optionally be used in the form of the individual optical isomers, mixtures of the individual enantiomers, or racemates. They are particularly preferably used in the form of the enantiomerically pure compounds, while the compounds of formula 1, wherein the asymmetric carbon centre "—CH(OH)—" benzylic to the phenyl ring is in the R-configuration. The particularly preferred R-enantiomers of the compounds of general formula 1 may be represented by general formula R-1,

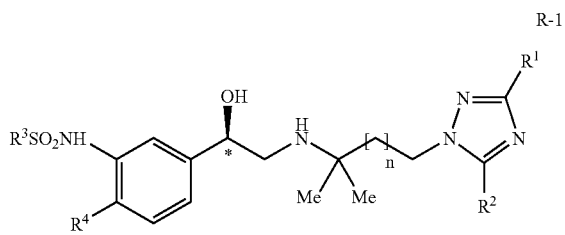

wherein the groups $R^1$, $R^2$, $R^3$, $R^4$ and n may have the meanings given above.

By acid addition salts with pharmacologically acceptable acids are meant, for example, the salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate, and hydromethanesulphonate.

Halogen within the scope of the present invention denotes fluorine, chlorine, bromine, or iodine. Unless stated otherwise, fluorine and bromine are the preferred halogens, while fluorine is generally preferred.

Unless otherwise stated, the alkyl groups (alkyl) are straight-chained or branched alkyl groups having 1 to 6, preferably 1 to 4 carbon atoms. The following are mentioned by way of example: methyl, ethyl, propyl, or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Examples of alkylene groups (alkylene), unless otherwise stated, are branched and unbranched alkylene groups with 1 to 6, preferably 1 to 4 carbon atoms. The following are mentioned by way of example: methylene, ethylene, propylene or butylene. Unless stated otherwise, the definitions propylene and butylene include all the possible isomeric forms of the groups in question.

Examples of alkenylene groups (alkenylene), unless otherwise stated, are branched and unbranched alkenylene groups with 1 to 6, preferably 1 to 4 carbon atoms. The following are mentioned by way of example: ethenylene, propenylene or butenylene.

Examples of cycloalkyl groups (cycloalkyl), unless otherwise stated, are cyclic alkyl groups with 3 to 6. The following are mentioned by way of example: cyclopropyl, cyclobutanyl, cyclopentyl or cyclohexyl.

Examples of alkyloxy groups (O-alkyl), unless otherwise stated, are branched and unbranched alkyl groups with 1 to 6, preferably 1 to 4 carbon atoms, linked via an oxygen atom. The following are mentioned by way of example: methyloxy, ethyloxy, propyloxy, or butyloxy. In some cases the abbreviations -OMe, -OEt, -Oprop, or -OBu are used to denote the groups methyloxy, ethyloxy, propyloxy, or butyloxy. Unless stated otherwise, the definitions propyloxy and butyloxy include all the possible isomeric forms of the groups in question. Thus, for example, propyloxy includes n-propyloxy and iso-propyloxy, and butyloxy includes iso-butyloxy, sec-butyloxy, and tert-butyloxy, etc. In some cases, within the scope of the present invention, the term alkoxy may be used instead of the term alkyloxy. The groups methyloxy, ethyloxy, propyloxy, or also butyloxy may optionally also be referred to as methoxy, ethoxy, propoxy, or butoxy.

Examples of halogenoalkylene (haloalkyl) groups, unless otherwise stated, are branched and unbranched alkyl groups with 1 to 6 carbon atoms, wherein one or more hydrogen atoms are replaced by halogen atoms, preferably by fluorine. The following are mentioned for example: $CHF_2$, $CF_3$, $CH_2CF_3$, and $CF_2CF_3$.

Suitable aryl groups, unless otherwise stated, are aromatic ring systems with 6 to 10 carbon atoms. Preferred aryl groups are phenyl and naphthyl, while phenyl is particularly preferred according to the invention.

Examples of heterocyclic groups (heterocycles), unless otherwise stated, are aromatic or non-aromatic ring systems with 2 to 5 carbon atoms and 1, 2, or 3 atoms selected from among O, S, or N, preferably N. Particularly preferred heterocycles are piperidine, piperazine, morpholine, pyrolidine, pyrrole, imidazole, triazole, pyridine, pyrimidine, thiophene, tetrahydrofuran, or furan.

The compounds according to the invention may be prepared analogously to methods already known in the art. Suitable methods of preparation are known for example from EP 43 940 or from WO 01/83462, which applications are incorporated herein in their entireties.

The examples of synthesis described below serve to illustrate new compounds according to the invention in more detail. However, they are intended only as examples of procedures to illustrate the invention without restricting it to the subject matter described in an exemplifying capacity hereinafter.

Intermediate Product 1: 1,1-dimethyl-3-(5-methyl-3-p-tolyl-[1,2,4]triazol-1-yl]-propylamine

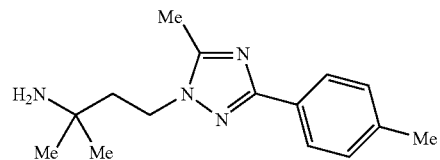

a) 4-methyl-benzoic acid-(1-imino-ethyl)-hydrazide 1.65 g (72 mmol) sodium are dissolved in 80 mL ethanol. 8.89 g (72 mmol) ethylacetimidate hydrochloride in 160 mL ethanol are added at ambient temperature and the precipitated sodium chloride is filtered off. The filtrate is combined with 6.00 g (40 mmol) 4-methyl-benzoic acid hydrazide and stirred overnight. The reaction mixture is evaporated down and cooled. The precipitated solid is filtered off and washed with cold ethanol and diethyl ether (5.7 g white solid). A further 1.2 g of solid are obtained from the filtrate after distillation of the solvent and recrystallisation from ethanol.

Yield: 6.93 g (91%); mass spectroscopy $[M+H]^+=192$.

b) 5-methyl-3-p-tolyl-[1,2,4]triazole 7.58 g (40 mmol) 4-methyl-benzoic acid-(1-imino-ethyl)-hydrazide are heated to 180° C. for 30 minutes with stirring. After cooling the solid is dissolved in chloroform.

The precipitate formed on cooling is suction filtered and recrystallised from chloroform.

Yield: 4.82 g (70%); mass spectroscopy [M+H]$^+$=174.

c) tert-butyl[1,1-dimethyl-3-(5-methyl-3-p-tolyl-[1,2,4]triazol-1-yl)-propyl]-carbamate 1.35 g (34 mmol, 60%) sodium hydride are added at 0° C. to a solution of 4.87 g (28 mmol) 5-methyl-3-p-tolyl-[1,2,4] triazole in 40 mL DMPU. The reaction mixture is heated to ambient temperature and then stirred for one hour. 9.35 g (42 mmol) tert-butyl (3-chloro-1,1-dimethyl-propyl)-carbaminate and 1.87 g (5 mmol) tetrabutylammonium iodide are added and the mixture is stirred overnight at ambient temperature and then for another 2 hours at 80° C. It is combined with water and ethyl acetate, the aqueous phase is separated off and extracted with ethyl acetate. The combined organic phases are washed with water and sodium chloride solution, dried with sodium sulphate and evaporated down. The residue is purified by column chromatography (silica gel; petroleum ether/ethyl acetate=1:1). Oil.

Yield: 2.97 g (30%); mass spectroscopy [M+H]$^+$=359.

d) 1,1-dimethyl-3-(5-methyl-3-p-tolyl-[1,2,4]triazol-1-yl]-propylamine

A total of 11 mL trifluoroacetic acid are added dropwise to a solution of 2.97 g (8.3 mmol) tert-butyl[1,1-dimethyl-3-(5-methyl-3-p-tolyl-[1,2,4]triazol-1-yl)-propyl]-carbamate in 80 mL dichloromethane and the mixture is stirred overnight at ambient temperature. The solvent is distilled off and the residue is combined with diethyl ether and stirred. The precipitated solid is filtered off and washed.

Yield: 2.11 g (68%, trifluoroacetate); mass spectroscopy [M+H]$^+$=259.

Intermediate Product 2: 3-[3-(4-fluoro-phenyl)-5-methyl-[1,2,4]triazol-1-yl]-1,1-dimethyl-propylamine

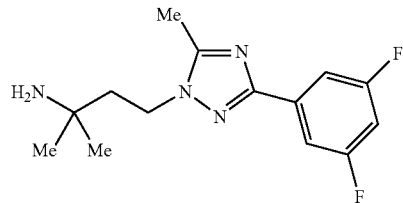

a) 4-fluoro-benzoic acid-(1-imino-ethyl)-hydrazide

Prepared from 7.2 g (58 mmol) ethylacetimidate hydrochloride and 5.00 g (32 mmol) 4-fluoro-benzoic acid hydrazide analogously to the method described for intermediate product 1, Step a).

Yield: 5.78 g (91%); mass spectroscopy [M+H]$^+$=196.

b) 3-(4-fluoro-phenyl)-5-methyl-[1,2,4]triazole

The product is prepared analogously to the method described for intermediate product 1 b) from 5.77 g (30 mmol) 4-fluoro-benzoic acid-(1-imino-ethyl)-hydrazide.

Yield: 4.11 g (78%); mass spectroscopy [M+H]$^+$=178.

c) tert-butyl {3-[3-(4-fluoro-phenyl)-5-methyl-[1,2,4]triazol-1-yl]-1,1-dimethyl-propyl}-carbamate 5.88 g (33 mmol) 3-(4-fluoro-phenyl)-5-methyl-[1,2,4] triazole are dissolved in 40 mL DMPU and reacted with 11.04 g (50 mmol) tert-butyl(3-chloro-1,1-dimethyl-propyl)-carbamate, 1.59 g (40 mmol, 60%) sodium hydride and 2.21 g (6 mmol) tetrabutylammonium iodide as described for intermediate product 1c).

Yield: 4.22 g (35%); mass spectroscopy [M+H]$^+$=363.

d) 3-[3-(4-fluoro-phenyl)-5-methyl-[1,2,4]triazol-1-yl]-1,1-dimethyl-propylamine Obtained by reacting 4.22 g (11.6 mmol) tert-butyl {3-[3-(4-fluoro-phenyl)-5-methyl-[1,2,4]triazol-1-yl]-1,1-dimethyl-propyl}-carbamate in 100 mL dichloromethane and 15 mL trifluoroacetic acid. White solid.

Yield: 4.43 g (trifluoroacetate); mass spectroscopy [M+H]$^+$=263.

Intermediate Product 3: 3-[3-(3,5-difluoro-phenyl)-5-methyl-[1,2,4]triazol-1-yl]-1,1-dimethyl-propylamine

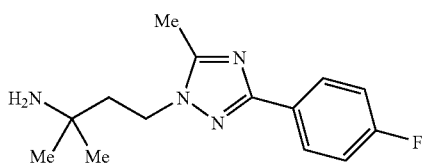

a) 3,5-difluoro-benzoic acid-(1-imino-ethyl)-hydrazide

The compound is obtained analogously to the method described for intermediate product 1a) from 4.91 g (40 mmol) ethylacetimidate hydrochloride and 3.80 g (22 mmol) 3,5 difluoro-benzoic acid hydrazide.

Yield: 4.49 g (95%); mass spectroscopy [M+H]$^+$=214.

b) 3-(3,5-difluoro-phenyl)-5-methyl-[1,2,4]triazole

Prepared from 4.61 g (22 mmol) 3,5-difluoro-benzoic acid-(1-imino-ethyl)-hydrazide.

Yield: 3.81 g (91%); mass spectroscopy [M+H]$^+$=196.

c) tert-butyl {3-[3-(3,5-difluoro-phenyl)-5-methyl-[1,2,4]triazol-1-yl]-1,1-dimethyl-propyl}-carbamate 3.74 g (19 mmol) 3-(3,5-difluoro-phenyl)-5-methyl-[1,2,4]triazole in 25 mL DMPU are reacted with 0.92 g (23 mmol, 60%) sodium hydride, 6.37 g (29 mmol) tert-butyl(3-chloro-1,1-dimethyl-propyl)-carbamate and 1.27 g (3.5 mmol) tetrabutylammonium iodide analogously to Example 1c). Oil.

Yield: 2.62 g (36%); mass spectroscopy [M+H]$^+$=381.

d) 3-[3-(3,5-difluoro-phenyl)-5-methyl-[1,2,4]triazol-1-yl]-1,1-dimethyl-propylamine 2.62 g (6.9 mmol) tert-butyl {3-[3-(3,5-difluoro-phenyl)-5-methyl-[1,2,4]triazol-1-yl]-1,1-dimethyl-propyl}-carbamate in 65 mL dichloromethane are reacted with 9 mL trifluoroacetic acid in the manner described for intermediate product 1d). White solid.

Yield: 2.11 g (trifluoroacetate); mass spectroscopy [M+H]$^+$=281.

Intermediate Product 4: 3-[5-ethyl-3-(4-methoxy-phenyl)-[1,2,4]triazol-1-yl]-1,1-dimethyl-propylamine

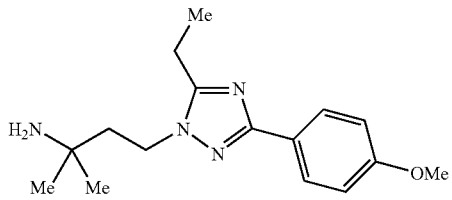

a) 4-methoxy-benzoic acid-(1-imino-propyl)-hydrazide

Prepared from 4.90 g (45 mmol) propioamidine hydrochloride and 5.00 g (30 mmol) 4-methoxy-benzoic acid hydrazide analogously to the method described for intermediate product 1a). After the ethanol has been distilled off, 10.0 g crude product is obtained that is reacted without any further purification.

b) 5-ethyl-3-(4-methoxy-phenyl)-[1,2,4]triazole 9.99 g (60%, approx. 28 mmol) 4-methoxy-benzoic acid-(1-imino-propyl)-hydrazide are heated to 150° C. for two hours. After cooling the melt is purified by chromatography on a silica gel column (petroleum ether/ethyl acetate=3/7). Light yellow solid.

Yield: 4.56 g (75% over two steps); mass spectroscopy [M+H]$^+$=204.

c) tert-butyl{3-[5-ethyl-3-(4-methoxy-phenyl)-[1,2,4]triazol-1-yl]-1,1-dimethyl-propyl-carbamate 4.30 g (21.2 mmol) 5-ethyl-3-(4-methoxy-phenyl)-[1,2,4] triazole are dissolved in 30 mL DMPU and cooled to 0° C. Under a protective gas atmosphere 1.02 g (24 mmol, 60%) sodium hydride are then added batchwise and the reaction mixture is slowly heated to ambient temperature and then stirred for one hour. 6.10 g (27.5 mmol) tert-butyl (3-chloro-1,1-dimethyl-propyl)-carbamate and 1.41 g (3.8 mmol) tetrabutylammonium iodide are added. The mixture is stirred overnight and the reaction is then stopped by the addition of water and ethyl acetate. The aqueous phase is separated off and extracted with ethyl acetate. The combined organic phases are washed with sodium chloride solution, dried with sodium sulphate and evaporated down. The oil remaining is purified by chromatography on a silica gel column (petroleum ether/ethyl acetate=3:7).

Yield: 6.82 g (83%); mass spectroscopy [M+H]$^+$=389.

d) 3-[5-ethyl-3-(4-methoxy-phenyl)-[1,2,4]triazol-1-yl]-1,1-dimethyl-propylamine A total of 20 mL trifluoroacetic acid are added dropwise to a solution of 6.81 g (17.5 mmol) tert-butyl {3-[5-ethyl-3-(4-methoxy-phenyl)-[1,2,4]triazol-1-yl]-1,1-dimethyl-propyl-carbamate in 150 mL dichloromethane. After three hour's stirring at ambient temperature the solution is evaporated down and the oil remaining is combined with diethyl ether. The precipitated white solid is filtered off, washed with diethyl ether and dried.

Yield: 7.86 g (trifluoroacetate); mass spectroscopy [M+H]$^+$=289.

Intermediate Product 5: methyl 3-[1-(3-amino-3-methyl-butyl)-5-methyl-1H-[1,2,4]triazol-3-yl]-benzoate

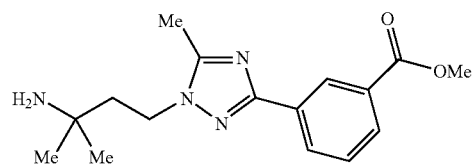

a) methyl 3-[N'-benzyloxycarbonyl-hydrazinocarbonyl)-benzoate 10.80 g (54.4 mmol) methyl 3-chlorocarbonyl-benzoate in 100 mL diethyl ether are added dropwise to a solution of 9.04 g (54.4 mmol) benzyl hydrazinecarboxylate in 100 mL diethyl ether, 100 mL dichloromethane and 4.83 mL pyridine while being cooled with an ice bath. The reaction mixture is stirred overnight at ambient temperature and then combined with water. The precipitated solid is filtered off and washed with diethyl ether. White solid.

Yield: 14.1 g (79%); mass spectroscopy [M−H]$^+$=327.

b) methyl 3-hydrazinocarbonyl-benzoate 14.6 g (44.5 mmol) methyl 3-[N'-benzyloxycarbonyl-hydrazinocarbonyl)-benzoate are dissolved in 75 mL methanol and hydrogenated in the presence of palladium on charcoal (10%) at ambient temperature and 3 bar hydrogen pressure. The catalyst is filtered off and the filtrate is freed from solvent. White solid.

Yield: 7.98 g (92%); mass spectroscopy [M+H]$^+$=195.

c) methyl 3-[N'-(1-imino-ethyl)-hydrazinocarbonyl]-benzoate

Prepared analogously to the method described for intermediate product 1a) from methyl 3-hydrazinocarbonyl-benzoate and ethylacetimidate hydrochloride. White solid.

Yield: 8.60 g (90%); mass spectroscopy [M+H]$^+$=236.

d) methyl 3-(5-methyl-1H-[1,24]triazol-3-yl)-benzoate 8.10 g (34.4 mmol) methyl 3-[N'-(1-imino-ethyl)-hydrazinocarbonyl]-benzoate are heated to 180° C. for 30 minutes. 80 mL chloroform are added to the solid obtained after cooling. The suspension is filtered and the product is dried. White solid.

Yield: 4.03 g (55%); mass spectroscopy [M+H]$^+$=218.

e) methyl 3-[1-(3-tert-butoxycarbonylamino-3-methyl-butyl)-5-methyl-1H-[1,2,4]triazol-3-yl-benzoate 6.00 g (27.6 mmol) methyl 3-(5-methyl-1H-[1,24]triazol-3-yl)-benzoate and 9.19 g (41.4 mmol) tert-butyl(3-chloro-1, 1-dimethyl-propyl)-carbamate are reacted and worked up in the manner described for intermediate product 1c). Yellow oil.

Yield: 5.96 g (54%); mass spectroscopy [M+H]⁺=403.

f) methyl 3-[1-(3-amino-3-methyl-butyl)-5-methyl-1H-[1,2,4]triazol-3-yl]-benzoate Obtained from methyl 3-[1-(3-tert-butoxycarbonylamino-3-methyl-butyl)-5-methyl-1H-[1,2,4]triazol-3-yl-benzoate analogously to the method described for intermediate product 1d).

Yield: 5.36 g (68%, di-trifluoroacetate); mass spectroscopy [M+H]⁺=303.

The following intermediate products may also be obtained analogously using the methods of synthesis described.

Intermediate Product 6: 3-[5-methyl-3-(2-methoxy-phenyl)-[1,2,4]triazol-1-yl]-1,1-dimethyl-propylamine

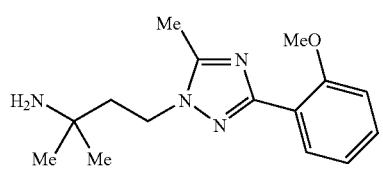

Intermediate Product 7: 3-[5-methyl-3-(4-methoxy-phenyl)-[1,2,4]triazol-1-yl]-1,1-dimethyl-propylamine

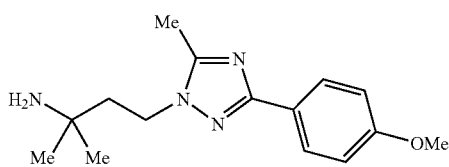

Intermediate Product 8: 3-[5-methyl-3-(3-benzo[1,3]dioxol-5-yl)-[1,2,4]triazol-1-yl]-1,1-dimethyl-propylamine

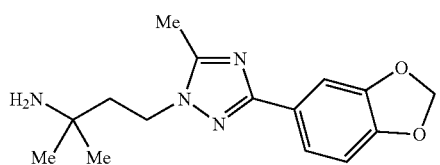

Intermediate Product 9: 2-[3-(4-methoxy-phenyl)-[1,2,4]triazol-1-yl]-1,1-dimethyl-ethylamine

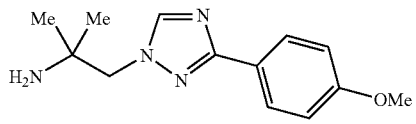

Intermediate Product 10: 1,1,-dimethyl-3-([1,2,4]triazol-1-yl)-propylamine

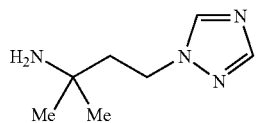

General Method 1 (AAV1):

1 mmol of N-[2-benzyloxy-5-[2-ethoxy-2-hydroxy-acetyl)-phenyl]-methanesulphonamide and 1 mmol of amine (or intermediate product) are stirred for 30 minutes in 5 mL tetrahydrofuran at ambient temperature. The mixture is cooled to 0° C. and 1.5 mL of a 2 molar solution of lithium borohydride in tetrahydrofuran are added dropwise under an argon atmosphere. The mixture is stirred for 15 min at 0° C., combined with 10 mL dichloromethane and 3 mL water, stirred for a further hour at ambient temperature and then filtered through kieselguhr, eluting with dichloromethane. The eluate is freed from solvent and the residue, if necessary, is purified by chromatography. The benzyl ether thus obtained is dissolved in methanol and hydrogenated with palladium on charcoal (10%) as catalyst at 2.5 bar and ambient temperature. Then the catalyst is separated off and the crude product is purified by chromatography (reverse phase, acetonitrile/water gradient with 0.1% trifluoroacetic acid).

EXAMPLE 1

N-[5-(2-{3-[5-ethyl-3-(4-methoxy-phenyl)-[1,2,4]triazol-1-yl]-1,1-dimethyl-propylamino}-1-hydroxy-ethyl)-2-hydroxy-phenyl]-methanesulphonamide

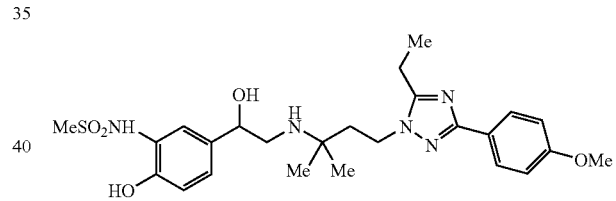

Prepared according to AAV1 from N-[2-benzyloxy-5-[2-ethoxy-2-hydroxy-acetyl)-phenyl]-methanesulphonamide and 3-[5-ethyl-3-(4-methoxy-phenyl)-[1,2,4]triazol-1-yl]-1,1-dimethyl-propylamine.

Yield: 255 mg (40% over 2 steps, trifluoroacetate); mass spectroscopy: [M+H]⁺=518.

EXAMPLE 2

N-[5-(2-{1,1-dimethyl-3-[5-methyl-3-(4-trifluoromethyl-phenyl)-[1,2,4]triazol-1-yl]-propylamino}-1-hydroxy-ethyl)-2-hydroxy-phenyl]-methanesulphonamide

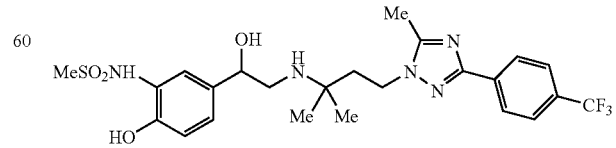

Obtained according to AAV1 by reacting N-[2-benzyloxy-5-[2-ethoxy-2-hydroxy-acetyl)-phenyl]-methanesulphonamide and 1,1-dimethyl-3-[5-methyl-3-(4-trifluoromethyl-phenyl)-[1,2,4]triazol-1-yl]-propylamine. White solid.

Yield: 78 mg (12% over 2 steps, trifluoroacetate); mass spectroscopy: [M+H]$^+$=541.

EXAMPLE 3

N-(5-{2-[1,1-dimethyl-3-(5-methyl-3-p-tolyl-[1,2,4]triazol-1-yl)-propylamino]-1-hydroxy-ethyl}-2-hydroxy-phenyl)-methanesulphonamide

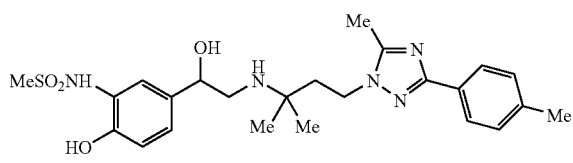

Obtained according to AAV1 from N-[2-benzyloxy-5-[2-ethoxy-2-hydroxy-acetyl)-phenyl]-methanesulphonamide and 1,1-dimethyl-3-(5-methyl-3-p-tolyl-[1,2,4]triazol-1-yl)-propylamine. White solid.

Yield: 7 mg (1% over 2 steps, trifluoroacetate); mass spectroscopy: [M+H]$^+$=488.

EXAMPLE 4

N-[5-(2-{3-[3-(4-fluoro-phenyl)-5-methyl-[1,2,4]triazol-1-yl]-1,1-dimethyl-propylamino)-1-hydroxy-ethyl)-2-hydroxy-phenyl]-methanesulphonamide

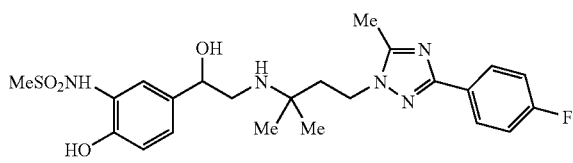

Prepared from N-[2-benzyloxy-5-[2-ethoxy-2-hydroxy-acetyl)-phenyl]-methanesulphonamide and 3-[3-(4-fluoro-phenyl)-5-methyl-[1,2,4]triazol-1-yl]-1,1-dimethyl-propylamine according to AAV1. White solid.

Yield: 155 mg (26% over 2 steps, trifluoroacetate); mass spectroscopy: [M+H]$^+$=492.

EXAMPLE 5

3-(1-{3-[2-hydroxy-2-(4-hydroxy-3-methanesulphonylamino-phenyl)-ethylamino]-3-methyl-butyl}-5-methyl-1H-[1,2,4]triazol-3-yl)-benzoate methyl

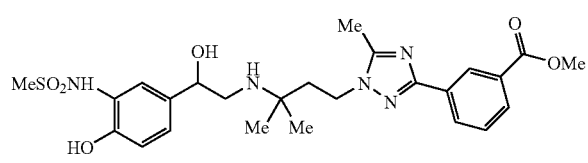

Prepared according to AAV1 from N-[2-benzyloxy-5-[2-ethoxy-2-hydroxy-acetyl)-phenyl]-methanesulphonamide and methyl 3-[1-(3-amino-3-methyl-butyl)-5-methyl-1H-[1,2,4]triazol-3-yl]-benzoate. White solid.

Yield: 36 mg (7% over 2 steps, trifluoroacetate); mass spectroscopy: [M+H]$^+$=532.

EXAMPLE 6

N-[5-(2-{3-[3-(3,5-difluoro-phenyl)-5-methyl-[1,2,4]triazol-1-yl]-1,1-dimethyl-propylamino}-1-hydroxy-ethyl)-2-hydroxy-phenyl]-methanesulphonamide

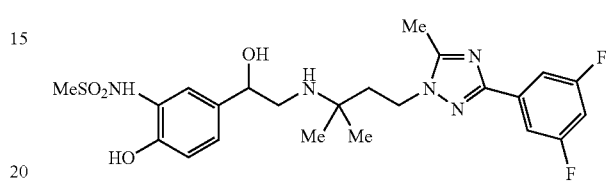

Prepared according to AAV1 from N-[2-benzyloxy-5-[2-ethoxy-2-hydroxy-acetyl)-phenyl]-methanesulphonamide and 3-[3-(3,5-difluoro-phenyl)-5-methyl-[1,2,4]triazol-1-yl]-1,1-dimethyl-propylamine. White solid.

Yield: 20 mg (3% over 2 steps, trifluoroacetate); mass spectroscopy: [M+H]$^+$=510.

EXAMPLE 7

N-[2-hydroxy-5-(1-hydroxy-2-{3-[3-(2-methoxy-phenyl)-5-methyl-[1,2,4]triazol-1-yl]-1,1-dimethyl-propylamino}-ethyl)-phenyl]-methanesulphonamide

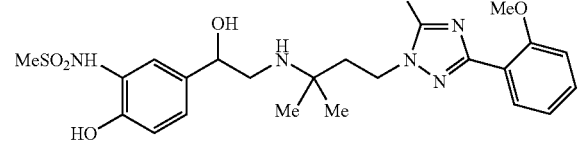

347 mg (1 mmol) 3-[3-(2-methoxy-phenyl)-5-methyl-[1,2,4]triazol-1-yl]-1,1-dimethyl-propylamine hydrochloride are combined with sodium hydroxide solution and stirred for 2 hours at ambient temperature. The solution is added to kieselguhr and eluted with dichloromethane. The eluate is evaporated down and the residue is taken up in 5 mL THF. 379 mg (1 mmol) N-[2-benzyloxy-5-[2-ethoxy-2-hydroxy-acetyl)-phenyl]-methanesulphonamide are added and the mixture is stirred for 30 min at ambient temperature. After cooling to 0° C. 1.5 mL of a 2 molar solution of lithium borohydride in THF are added dropwise and the mixture is stirred for 30 minutes at ambient temperature. The reaction mixture is combined with 10 mL dichloromethane and 3 mL water, stirred for one hour and then filtered through kieselguhr with dichloromethane as eluant. The solvent is distilled off and the residue is taken up in 5 mL methanol. Then it is hydrogenated with 100 mg palladium on charcoal at 2.5 bar. The catalyst is separated off and the filtrate is evaporated down. For further purification the residue is chromatographed (RP, acetonitrile:water gradient with 0.1% trifluoroacetate).

Yield: 323 mg (52%, trifluoroacetate); mass spectrometry: [M+H]$^+$=504.

EXAMPLE 8

N-[2-hydroxy-5-(1-hydroxy-2-{3-[3-(4-methoxy-phenyl)-5-methyl-[1,2,4]triazol-1-yl]-1,1-dimethyl-propylamino}-ethyl)-phenyl]-methanesulphonamide

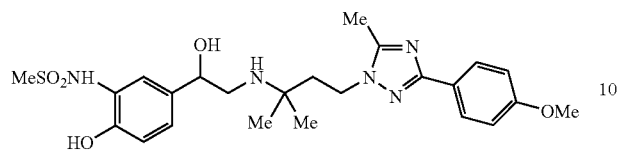

379 mg (1 mmol) of N-[2-benzyloxy-5-[2-ethoxy-2-hydroxy-acetyl)-phenyl]-methanesulphonamide and 274 mg (1 mmol) of 3-[3-(4-methoxy-phenyl)-5-methyl-[1,2,4]triazol-1-yl]-1,1-dimethyl-propylamine are suspended in 5 mL ethanol and heated to 70° C. The solution formed is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. It is filtered through aluminium oxide (basic), washed repeatedly with methylene chloride/methanol 15:1, evaporated down and chromatographed (silica gel; dichloromethane with 0-10% methanol: ammonia=9:1). The benzyl compound thus obtained is dissolved in 10 mL methanol and hydrogenated with palladium on charcoal at 2.5 bar hydrogen pressure. Then it is filtered and the filtrate is evaporated down.

Yield: 339 mg (67%); mass spectrometry: [M+H]$^+$=504.

EXAMPLE 9

N-(5-{2-[3-(3-benzo[1,3]dioxol-5-yl-5-methyl-[1,2,4]triazol-1-yl)-1,1-dimethyl-propylamino]-1-hydroxy-ethyl}-2-hydroxy-phenyl)-methanesulphonamide

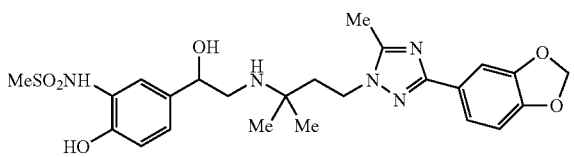

Analogously to the method described for Example 7, 379 mg (1 mmol) N-[2-benzyloxy-5-[2-ethoxy-2-hydroxy-acetyl)-phenyl]-methanesulphonamide and 288 mg (1 mmol) 3-(3-benzo[1,3]dioxol-5-yl-5-methyl-[1,2,4]triazol-1-yl)-1,1-dimethyl-propylamine are reacted with one another. The subsequent debenzylation yields the target compound.

Yield: 371 mg (72%); mass spectrometry: [M+H]$^+$=518.

EXAMPLE 10

N-[2-hydroxy-5-(1-hydroxy-2-{3-[3-(4-methoxy-phenyl)-[1,2,4]triazol-1-yl]-1,1-dimethyl-propylamino}-ethyl)-phenyl]-methanesulphonamide

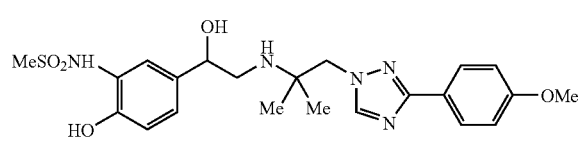

The target compound is obtained by reacting 379 mg (1 mmol) N-[2-benzyloxy-5-[2-ethoxy-2-hydroxy-acetyl)-phenyl]-methanesulphonamide and 246 mg (1 mmol) 2-[3-(4-methoxy-phenyl)-[1,2,4]triazol-1-yl]-1,1-dimethyl-ethylamine in the manner described for Example 7 followed by debenzylation.

Yield: 305 mg (64%); mass spectrometry: [M+H]$^+$=476.

EXAMPLE 11

N-{5-[2-[1,1-dimethyl-3-[1,2,4]triazol-1-yl-propylamino)-1-hydroxy-ethyl]-2-hydroxy-phenyl}-methanesulphonamide

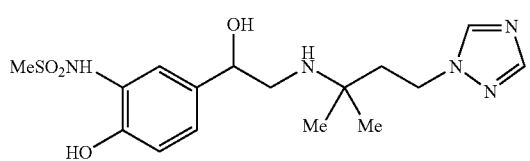

The target compound is prepared analogously to the methods described for Example 7 from 379 mg (1 mmol) N-[2-benzyloxy-5-[2-ethoxy-2-hydroxy-acetyl)-phenyl]-methanesulphonamide and 154 mg (1 mmol) 1,1-dimethyl-3-[1,2,4]triazol-1-yl-propylamine. Colourless solid.

Yield: 225 mg (59%); mass spectrometry: [M+H]$^+$=384.

As has been found, the compounds of formula 1 are characterized by their range of uses in the therapeutic field. Particular mention should be made of those applications for that the compounds of formula 1 according to the invention may preferably be used on the basis of their pharmaceutical activity as betamimetics. These include, for example, the treatment of inflammatory and obstructive respiratory complaints, selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome), and all forms of pulmonary oedema.

The compounds of formula 1 are preferably used for preparing a pharmaceutical composition for the treatment of obstructive pulmonary diseases selected from among bronchial asthma, paediatric asthma, severe asthma, acute asthma attacks, chronic bronchitis, and COPD (chronic obstructive pulmonary disease), while it is particularly preferable according to the invention to use them for preparing a pharmaceutical composition for the treatment of bronchial asthma and COPD.

It is also preferable to use the compounds of formula 1 for preparing a pharmaceutical composition for the treatment of pulmonary emphysema that has its origins in COPD or α1-proteinase inhibitor deficiency.

It is also preferable to use the compounds of formula 1 for preparing a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as, for example, lymphangiosis carcinomatosa, bronchoalveolar carcinoma, and lymphomas.

It is also preferable to use the compounds of formula 1 for preparing a pharmaceutical composition for the treatment of interstitial pulmonary diseases selected from among pneumonia caused by infections, such as, for example, infection by viruses, bacteria, fungi, protozoa, helminths or other pathogens, pneumonitis caused by various factors, such as for example aspiration and left heart insufficiency, radiation-induced pneumonitis or fibrosis, collagenoses, such, as for example, lupus erythematodes, systemic sclerodermy, or sarcoidosis, granulomatoses, such as, for example, Boeck's disease, idiopathic interstitial pneumonia or idiopathic pulmonary fibrosis (IPF).

It is also preferable to use the compounds of formula 1 for preparing a pharmaceutical composition for the treatment of cystic fibrosis or mucoviscidosis.

It is also preferable to use the compounds of formula 1 for preparing a pharmaceutical composition for the treatment of bronchitis, such as, for example, bronchitis caused by bacterial or viral infection, allergic bronchitis, and toxic bronchitis.

It is also preferable to use the compounds of formula 1 for preparing a pharmaceutical composition for the treatment of bronchiectasis.

It is also preferable to use the compounds of formula 1 for preparing a pharmaceutical composition for the treatment of ARDS (adult respiratory distress syndrome).

It is also preferable to use the compounds of formula 1 for preparing a pharmaceutical composition for the treatment of pulmonary oedema, for example, toxic pulmonary oedema after aspiration or inhalation of toxic substances and foreign substances.

It is particularly preferable to use the compounds of formula 1 for preparing a pharmaceutical composition for the treatment of asthma or COPD. Also of particular importance is the above-mentioned use for preparing a pharmaceutical composition for once-a-day treatment of inflammatory and obstructive respiratory complaints, particularly for the once-a-day treatment of asthma or COPD.

Suitable preparations for administering the compounds of formula 1 include, for example, tablets, capsules, suppositories, solutions, powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate, or lactose, disintegrants, such as corn starch or alginic acid, binders such as starch or gelatine, lubricants, such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers.

Similarly the tablet coating may consist of a number of layers to achieve delayed release, possibly using the excipients mentioned above for the tablets.

Syrups or elixirs containing the active substances or combinations of active substances according to the invention may additionally contain a sweetener, such as saccharine, cyclamate, glycerol, or sugar, and a flavour enhancer, e.g., a flavoring, such as vanillin or orange extract. They may also contain suspension adjuvants or thickeners, such as sodium carboxymethyl cellulose, wetting agents, such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates or stabilizers, such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may for example be prepared by mixing the active substances with inert carriers, such as lactose or sorbitol, and packing them into gelatine capsules. Suitable suppositories may be made, for example, by mixing with carriers provided for this purpose, such as neutral fats or polyethyleneglycol or the derivatives thereof.

Excipients that may be used include, for example, water, pharmaceutically acceptable organic solvents, such as paraffins (e.g., petroleum fractions), vegetable oils (e.g., groundnut or sesame oil), and mono- or polyfunctional alcohols (e.g., ethanol or glycerol), carriers, such as, e.g., natural mineral powders (e.g., kaolins, clays, talc, and chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch, and polyvinylpyrrolidone) and lubricants (e.g., magnesium stearate, talc, stearic acid, and sodium lauryl sulphate).

For oral use the tablets may obviously contain, in addition to the carriers specified, additives, such as sodium citrate, calcium carbonate, and dicalcium phosphate, together with various additional substances, such as starch, preferably potato starch, gelatin, and the like. Lubricants, such as magnesium stearate, sodium laurylsulphate, and talc may also be used to produce the tablets. In the case of aqueous suspensions, the active substances may be combined with various flavor enhancers or colourings in addition to the abovementioned excipients.

In the preferred use of the compounds of formula 1 for the treatment of asthma or COPD according to the invention it is particularly preferred to use preparations or pharmaceutical formulations that are suitable for inhalation. Inhalable preparations include inhalable powders, propellant-containing metered-dose aerosols, or propellant-free inhalable solutions. Within the scope of the present invention, the term propellant-free inhalable solutions also includes concentrates or sterile ready-to-use inhalable solutions. The formulations that may be used within the scope of the present invention are described in more detail in the next part of the specification.

An inhalable powder that may be formulated according to the invention may contain an active substance or compound of formula 1 either on its own or in admixture with suitable physiologically acceptable excipients.

If the active substance of formula 1 is present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextrans), polyalcohols (e.g., sorbitol, mannitol, xylitol), salts (e.g., sodium chloride, calcium carbonate), or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 μm. In some cases, it may seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronized active substance of formula 1, preferably with an average particle size of 0.5 to 10 μm, more preferably from 1 to 5 μm, is added to the excipient mixture. Processes for producing the inhalable powders according to the invention by grinding and micronizing and lastly mixing the ingredients together are known from the prior art. The inhalable powders according to the invention may be administered using inhalers known from the prior art.

The inhalation aerosols containing propellant gas according to the invention may contain the compounds of formula 1 dissolved in the propellant gas or in dispersed form. The compounds of formula 1 may be contained in separate formulations or in a common formulation, in which the compounds of formula 1 are either both dissolved, both dispersed, or in each case only one component is dissolved and the other is dispersed.

The propellant gases that may be used to prepare the inhalation aerosols are known from the prior art. Suitable propellant gases are selected from among hydrocarbons, such as n-propane, n-butane or isobutene, and halohydrocarbons, such as fluorinated derivatives of methane, ethane, propane, butane, cyclopropane or cyclobutane. The above-mentioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances of formula 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing compounds of formula 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric and sulphuric acids. It is also possible to use the acids that have already formed an acid addition salt with one of the active substances. Of the organic acids, ascorbic acid, fumaric acid, and citric acid are preferred. If desired, mixtures of the above acids may be used, particularly in the case of acids that have other properties in addition to their acidifying qualities, e.g., as flavorings, antioxidants, or complexing agents, such as citric acid or ascorbic acid, for example.

According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those that contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols, and polyoxyethylene fatty acid esters. The terms excipients and additives in this context denote any pharmacologically acceptable substance that is not an active substance, but that can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants, and/or preservatives that guarantee or prolong the shelf life of the finished pharmaceutical formulation, flavorings, vitamins, and/or other additives known in the art. The additives also include pharmacologically acceptable salts such as sodium chloride as isotonic agents.

The preferred excipients include antioxidants, such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those that are known in the art, particularly cetyl pyridinium chloride, benzalkonium chloride, or benzoic acid, or benzoates, such as sodium benzoate, in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance of formula 1, only benzalkonium chloride and sodium edetate. In another preferred embodiment, no sodium edetate is present.

The dosage of the compounds according to the invention is naturally highly dependent on the method of administration and the complaint that is being treated. When administered by inhalation the compounds of formula 1 are characterized by a high potency even at doses in the μg range. The compounds of formula 1 may also be used effectively above the μg range. The dosage may then be in the milligram range, for example.

In another aspect, the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

| Tablet | |
|---|---|
| | per tablet |
| active substance of formula 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, and then moistened with a solution of polyvinylpyrrolidone in water, kneaded, and then wet-granulated and dried. The granules, the remaining corn starch, and the magnesium stearate are screened and mixed together. The mixture is compressed to produce tablets of suitable shape and size.

| Tablet | |
|---|---|
| | per tablet |
| active substance of formula 1 | 80 mg |
| lactose | 55 mg |
| maize starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose, and polyvinylpyrrolidone are mixed together, The mixture is screened and worked with the remaining corn starch and water to form a granulate that is dried and screened. The sodium carboxymethyl starch and the magnesium stearate are added and mixed in and the mixture is compressed to form tablets of a suitable size.

| Ampoule solution | |
|---|---|
| active substance of formula 1 | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules that are then sterilized and sealed by fusion. The ampoules contain 5 mg, 25 mg and 50 mg of active substance.

| Metered-dose aerosol | |
|---|---|
| active substance of formula 1 | 0.005 |
| sorbitolan trioleate | 0.1 |
| monofluorotrichloromethane and TG134a:TG227 2:1 | ad 100 |

The suspension is transferred into a conventional aerosol container with a metering valve. Preferably, 50 µl of suspension are delivered per spray. The active substance may also be metered in higher doses if desired (e.g. 0.02% by weight).

| Powder for inhalation | |
|---|---|
| active substance of formula 1 | 12 µg |
| lactose monohydrate | ad 10 mg |

The powder for inhalation is produced in the usual way by mixing the individual ingredients together.

We claim:

1. A method for preparing a pharmaceutical composition comprising the steps of
   (a) providing a compound of formula 1

$$R^3SO_2NH \text{—Ar—CH(OH)—CH}_2\text{—NH—C(Me)}_2\text{—[CH}_2\text{]}_n\text{—N(triazole with } R^1, R^2\text{)}$$

wherein
   $R^1$ is hydrogen, —$C_{1-6}$-alkyl, —$C_{1-6}$-haloalkyl, —OH, —O—$C_{1-6}$-alkyl, halogen, aryl, or a heterocycle, wherein $R_1$ may be substituted by 1, 2, 3, 4, or 5 identical or different groups $R^5$;
   $R^5$ is halogen, —CN, —$NO_2$, —$C_{1-6}$-alkyl, —$C_{3-6}$-cycloalkyl, —$C_{1-6}$-haloalkyl, —CO—$R^6$, —COO—$R^6$, —CON—$R^{6}$-$R^7$, —O—$R^6$, —N—$R^{6}$—$R^7$, —N—$R^{6}$-CO—$R^7$, —N—$R_6$—$SO_2$—$R^7$, —S—$R^6$, —SO—$R^6$, —$SO_2$—$R^6$ or —$SO_2$N—$R^6$—$R^7$, —$C_{2-6}$-alkylene, —$C_{2-6}$-alkenylene, or —O—$C_{1-6}$-alkylene-O—;
   wherein $R^6$ and $R^7$ are individually hydrogen, —$C_{1-6}$-alkyl, or —$C_{3-6}$-cycloalkyl;
   $R^2$ is hydrogen, —$C_{1-6}$-alkyl, -or $C_{1-6}$-haloalkyl;
   $R^3$ is —$C_{1-6}$-alkyl;
   $R^4$ is —OH, —$NH_2$, or halogen; and
   n is 0, 1, 2, or 3;
or an isomer, enantiomer, or racemate thereof, in the form of a free base or an acid addition salt, and
   (b) combining said compound of the formula I with at least one excipient or additive to obtain the pharmaceutical composition.

2. The method according to claim 1, wherein $R_4$ denotes —OH.

3. The method of claim 1, wherein
   $R^1$ is hydrogen, —$C_{1-6}$-alkyl, —$C_{1-6}$-haloalkyl, —OH, —O—$C_{1-6}$-alkyl, halogen, or aryl,
   wherein $R^1$ may be substituted by 1, 2, 3, 4, or 5 identical or different groups $R^5$.

4. The method of claim 1, wherein
   $R^1$ is hydrogen, —$C_{1-6}$-alkyl, —O—$C_{1-6}$-alkyl, or aryl, wherein $R^1$ may be substituted by 1, 2, 3, 4, or 5 identical or different groups $R^5$;
   $R^2$ is hydrogen or —$C_{1-6}$-alkyl;
   $R^3$ is methyl; and
   $R^4$ is —OH.

5. The method of claim 1, wherein
R¹ is hydrogen or aryl that may be substituted by 1, 2, 3, 4, or 5 identical or different groups R⁵;
R² is hydrogen or —$C_{1-6}$-alkyl;
R³ is methyl; and
R⁴ is —OH.

6. The method of claim 1, wherein the compounds of formula 1 are used in the form of their R-enantiomers.

7. A compound of formula 1

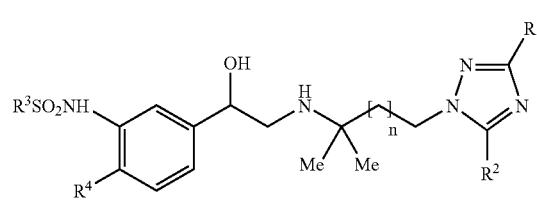

wherein
R¹ is hydrogen, —$C_{1-6}$-alkyl, —$C_{1-6}$-haloalkyl, —OH, —O—$C_{1-6}$-alkyl, halogen, aryl or a heterocycle, wherein $R_1$ may be substituted by 1, 2, 3, 4, or 5 identical or different groups R⁵;
R⁵ is halogen, —CN, —NO₂, —$C_{1-6}$-alkyl, —$C_{3-6}$-cycloalkyl, —$C_{1-6}$-haloalkyl, —CO—R⁶, —COO—R⁶, —CON—R⁶-R⁷, —O—R⁶, —N—R⁶-R⁷, —N—R⁶-CO—R⁷, —N—R⁶—SO₂—R⁷, —S—R⁶, —SO—R⁶ or —SO₂N—R⁷, —$C_{2-6}$-alkylene, —$C_{2-6}$-alkenylene, or —O—$C_{1-6}$-alkylene-O—;
R⁶ and R⁷ is hydrogen, —$C_{1-6}$-alkyl, or —$C_{3-6}$-cycloalkyl;
R² is hydrogen, —$C_{1-6}$-alkyl, -or $C_{1-6}$-haloalkyl;
R³ is methyl;
R⁴ is OH; and
n is 0, 1, 2, or 3;
or an isomer, enantiomer, or racemate thereof, in the form of a free base or an acid addition salt.

8. The compound according to claim 7, wherein R² is methyl or ethyl.

9. The compound according to claim 8, wherein n is 1.

10. The compound according to claim 9, wherein
R¹ denotes hydrogen or phenyl that may be substituted by 1, 2, or 3 identical or different groups R⁵.

11. The compound according to claim 10, wherein
R⁶ and R⁷ are individually hydrogen or —$C_{1-6}$-alkyl.

12. The compound according to claim 7, in the form of the R-enantiomers of formula R-1.

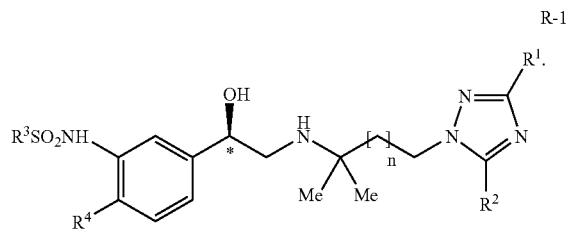

13. A pharmaceutical formulation comprising a compound of formula 1

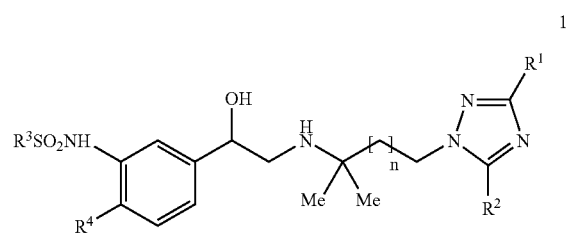

wherein
R¹ is hydrogen, —$C_{1-6}$-alkyl, —$C_{1-6}$-haloalkyl, —OH, —O—$C_{1-6}$-alkyl, halogen, aryl or a heterocycle, wherein R¹ may be substituted by 1, 2, 3, 4, or 5 identical or different groups R⁵;
R⁵ is halogen, —CN, —NO₂, —$C_{1-6}$-alkyl, —$C_{3-6}$-cycloalkyl, —$C_{1-6}$-haloalkyl, —CO—R⁶, —COO—R⁶, —CON—R⁶-R⁷, —O—R⁶, —N—R⁶-R⁷, —N—R⁶-R⁶-CO—R⁷, —N—R⁶—SO₂—R⁷, —S—R₆, —SO—R₆, —SO₂—R⁶ or —SO₂N—R⁶—R⁷, —$C_{2-6}$-alkylene, —$C_{2-6}$-alkenylene, or —O—$C_{1-6}$-alkylene-O—;
R⁶ and R⁷ are individually hydrogen, —$C_{1-6}$-alkyl, or —$C_{3-6}$-cycloalkyl;
R² is hydrogen, —$C_{1-6}$-alkyl, -or $C_{1-6}$-haloalkyl;
R³ is methyl;
R⁴ is OH; and
n is 0, 1, 2, or 3;
or an isomer, enantiomer, or racemate thereof, in the form of a free base or an acid addition salt.

14. The compound according to claim 7, wherein
R¹ is hydrogen or phenyl that may be substituted by 1, 2, or 3 identical or different groups R⁵;
R² is methyl or ethyl;
n is 1; and
R⁶ and R⁷ are individually hydrogen, or —$C_{1-6}$-alkyl.

15. The pharmaceutical formulation of claim 13, adapted for administration to a patient by inhalation.

16. The pharmaceutical formulation of claim 15, in the form of an inhalable powder, a propellant-containing metered-dose aerosol, or a propellant-free inhalable solution.

* * * * *